(12) United States Patent  
Morina

(10) Patent No.: US 12,390,257 B2  
(45) Date of Patent: Aug. 19, 2025

(54) SURGICAL FORCEPS FOR HOLDING TWO BONE PARTS

(71) Applicant: Gazmend Morina, Schwyz (CH)

(72) Inventor: Gazmend Morina, Schwyz (CH)

(73) Assignee: Gazmend Morina, Schwyz (CH)

( * ) Notice: Subject to any disclaimer, the term of this patent is extended or adjusted under 35 U.S.C. 154(b) by 257 days.

(21) Appl. No.: 18/043,638

(22) PCT Filed: Aug. 31, 2021

(86) PCT No.: PCT/IB2021/057933  
§ 371 (c)(1),  
(2) Date: Mar. 1, 2023

(87) PCT Pub. No.: WO2022/049479  
PCT Pub. Date: Mar. 10, 2022

(65) Prior Publication Data  
US 2023/0310049 A1 Oct. 5, 2023

(30) Foreign Application Priority Data  
Sep. 1, 2020 (DE) ............ 10 2020 122 829.5

(51) Int. Cl.  
*A61B 17/88* (2006.01)  
*A61B 17/16* (2006.01)  
(Continued)

(52) U.S. Cl.  
CPC ...... *A61B 17/8866* (2013.01); *A61B 17/2812* (2013.01); *A61B 17/2833* (2013.01);  
(Continued)

(58) Field of Classification Search  
CPC ............ A61B 17/8866; A61B 17/2812; A61B 17/2833; A61B 17/808; A61B 17/28; A61B 17/1606; A61B 17/1608; A61B 17/22031; A61B 17/29; A61B 17/2816; A61B 17/282; A61B 17/2841; A61B 17/44; A61B 17/80; A61B 17/7047; A61B 17/8061; A61B 17/1728; A61B 17/564; A61B 17/2909; A61B 2017/2808; A61B 2017/2837; A61B 2017/2904; A61B 2017/2825; A61B 2017/2926; A61B 2017/2946;  
(Continued)

(56) References Cited

U.S. PATENT DOCUMENTS

| 1,985,108 | A | * | 12/1934 | Rush | A61B 17/8866 |
| | | | | | 606/86 R |
| 2017/0281202 | A1 | * | 10/2017 | Hampp | A61B 34/20 |
| 2018/0168707 | A1 | * | 6/2018 | Shariati | A61B 17/8866 |

* cited by examiner

*Primary Examiner* — Marcela I. Shirsat

(57) ABSTRACT

The invention relates to surgical forceps for holding two bone parts of a fractured bone at a bone fracture site comprising a first forceps part extending in a radial direction and a second forceps part extending in the radial direction rotatably held in a rotational direction about a pivot via a lock on the first forceps part, each forceps part having a forceps head with a clamping section at one end in the radial direction such that the bone parts are clampable between the forceps heads at the clamping sections, characterised in that each forceps part has a shoulder between the clamping sections and the lock, extending transversely to the radial direction and transversely to the direction of rotation, against which a plate can be placed against the radial direction for osteosynthesis of the bone parts.

8 Claims, 8 Drawing Sheets

Figure 1:
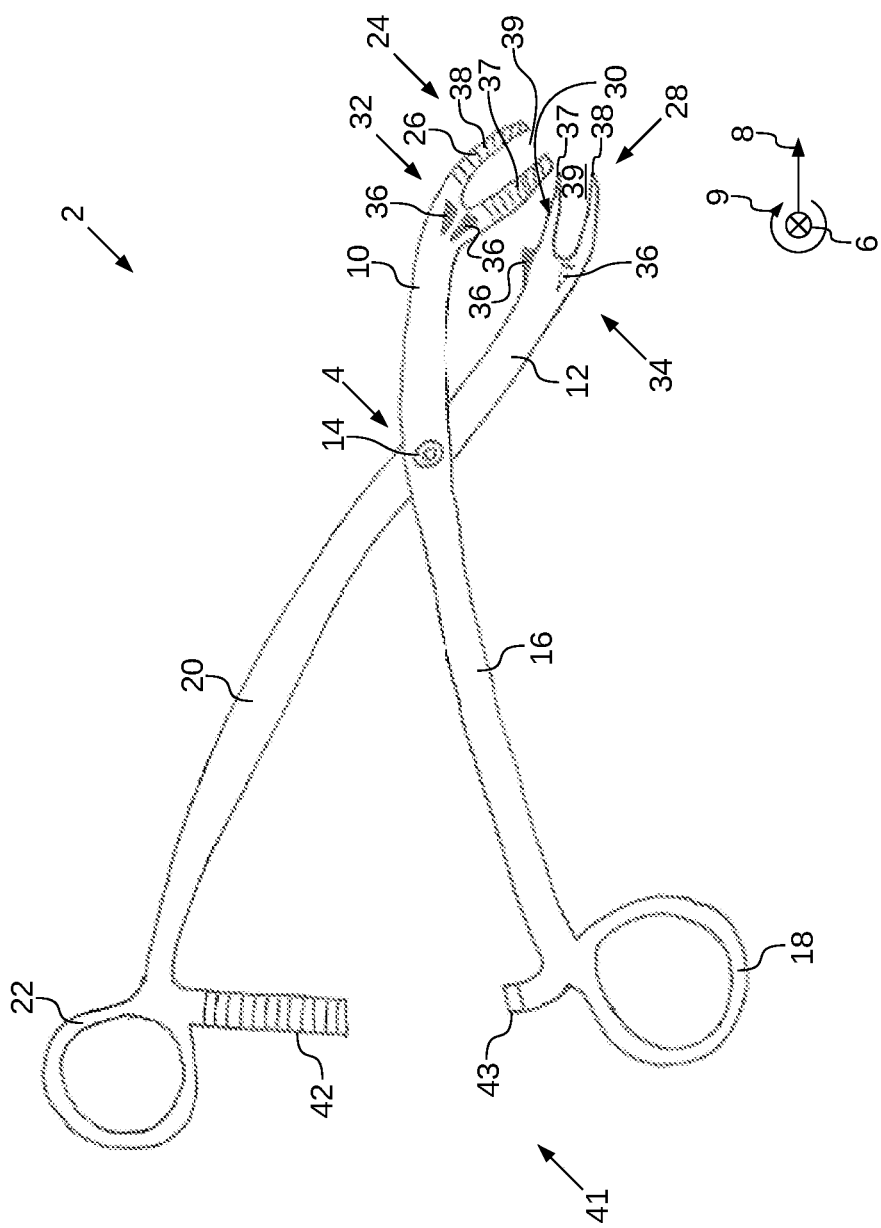

(51) Int. Cl.
*A61B 17/22* (2006.01)
*A61B 17/28* (2006.01)
*A61B 17/29* (2006.01)
*A61B 17/80* (2006.01)
*B25B 7/02* (2006.01)
*B25B 7/04* (2006.01)
*B25B 7/14* (2006.01)

(52) U.S. Cl.
CPC ........ *A61B 17/808* (2013.01); *A61B 17/1608* (2013.01); *A61B 17/22031* (2013.01); *A61B 17/2816* (2013.01); *A61B 17/282* (2013.01); *A61B 2017/2825* (2013.01); *A61B 2017/2837* (2013.01); *A61B 17/2841* (2013.01); *A61B 2017/2904* (2013.01); *B25B 7/02* (2013.01); *B25B 7/04* (2013.01); *B25B 7/14* (2013.01)

(58) Field of Classification Search
CPC .... A61B 2017/2947; A61B 2017/2945; B25B 7/00; B25B 7/02; B25B 7/04; B25B 7/14
USPC ...... 606/105, 915, 86 B, 99, 101, 86 R, 280, 606/281, 282, 53, 60
See application file for complete search history.

SURGICAL FORCEPS FOR HOLDING TWO BONE PARTS

CROSS REFERENCE OF RELATED APPLICATIONS

The present application is a 371 of international Application PCT/IB2021/057933, filed Aug. 31, 2021, which claims priority to DE 10 2020 122 829.5, filed on Sep. 1, 2020. The contents of each of the above-captioned patent applications are hereby expressly incorporated herein by reference in their entireties.

The present invention relates to a pair of forceps pursuant to the preamble of the valid claim 1.

Such surgical forceps, also called reduction forceps or repositioning forceps, are known from the patent document CN 102 166 132 A or from U.S. Pat. No. 1,985,108 A.

It is the object of the invention to improve the known surgical forceps.

The task is fulfilled by the characteristics of the independent claims. Preferred embodiments are the subject matter of the dependent claims.

In accordance with one aspect of the invention, surgical forceps for holding two bone parts of a fractured bone at a bone fracture site comprise a first forceps part extending in a radial direction and a second forceps part extending in the radial direction rotatably held in a rotational direction about a pivot via a lock on the first forceps part, each forceps part having a forceps head with a clamping section at one end in the radial direction such that the bone parts are clampable between the forceps heads at the clamping sections. According to the invention, each forceps part has a shoulder between the clamping sections and the lock, extending transversely to the radial direction and transversely to the direction of rotation, against which a plate can be placed for osteosynthesis of the bone parts against the radial direction.

The invention is based on the idea that several tools and/or hands are conventionally required for the repositioning of bones. Thus, in addition to the possible pre-drilling of a bone and the placement of a Kirschner wire, on the one hand the bone parts have to be positioned correctly and on the other hand the osteosynthesis material has to be placed correctly. Traditionally, different surgical forceps are used for both tasks. With the surgical forceps mentioned at the beginning, correctly positioned bone parts can be clamped and fixed at the same time as the osteosynthesis material, but several hands and/or tools are still required for the correct positioning of the bone parts and simultaneous correct placement of the osteosynthesis material, i.e. until the actual clamping process.

With the specified surgical forceps, it is proposed to clamp the bone parts not simultaneously with the osteosynthesis material but one after the other. For this purpose, the shoulder is used, which secures the position of the osteosynthesis material in a different direction than the clamping direction of the clamping sections of the surgical forceps. In this way, a single tool can be used first to correctly fix the position of the bone parts and then to determine the position of the osteosynthesis material simultaneously with the application of the surgical forceps. Therefore, by using the specified surgical forceps, the number of surgical tools can be reduced.

In one embodiment, the specified surgical forceps comprise a spacer in each clamping section in front of the shoulder as viewed in the radial direction, which is arranged to maintain a predetermined minimum distance between the bone parts and the shoulder. On the one hand, the minimum distance allows the position of the osteosynthesis material on the fixed bone parts to be adjusted, but with a certain mechanical play, which allows the relative position of the osteosynthesis material on the bone parts fixed against each other to be corrected as desired before screwing.

In a preferred embodiment of the specified surgical forceps, the spacer is formed in such a way that the clamping sections run towards each other in areas in front of the shoulders, as seen in the radial direction. In this way, the spacer can be formed in one piece with the clamping sections and thus integrated cost-effectively into the surgical forceps.

In another embodiment of the specified surgical forceps, the shoulders are formed as projections directed towards each other between the at least one clamping section and the lock. The projections can be attached as desired either integrally with the surgical forceps or as extra elements to already existing surgical forceps, so that the idea behind the specified surgical forceps can in principle also be realized on conventional surgical forceps by modification.

In a particularly preferred embodiment of the specified surgical forceps, at least two projections are arranged next to one another in the at least one clamping section to form the shoulder. In this way, the individual projections can be made smaller and thus more easily formed into the surgical forceps, for example, already during casting.

In yet another embodiment of the specified surgical forceps, each forceps head has, in the region of its clamping section, a recess which runs counter to the radial direction and separates the clamping section into a first fork tine and a second fork tine, and wherein the fork tines of one clamping section are thinner than the fork tines of the other clamping section, as viewed transversely to the radial direction and transversely to the direction of rotation.

In an additional embodiment of the specified surgical forceps, the thinner fork tines are arranged on a side opposite the screw-in side of a fixation screw for osteosynthesis of the bone parts. In this way, a screw can be guided obliquely through the recess and thus through the bone to be repositioned in a simple manner.

In a further embodiment of the specified surgical forceps, the fork tines are elastic in the direction of rotation with a modulus of elasticity between 30 GPa and 100 GPa. In this range of elasticity, the fork tines can easily compensate for unevenness of the bone and still apply sufficient compressive force to securely hold the bone parts.

In a still further embodiment of the specified surgical forceps, the fork tines are tapered in the radial direction. In this way, the tissue can be better protected when using the specified surgical forceps.

In an additional embodiment of the specified surgical forceps, the contact areas differ in their surface roughness, allowing the specified surgical forceps to be positioned well with one of the two clamping sections, while the other of the two clamping sections provides positional stability during clamping.

Figure 2:
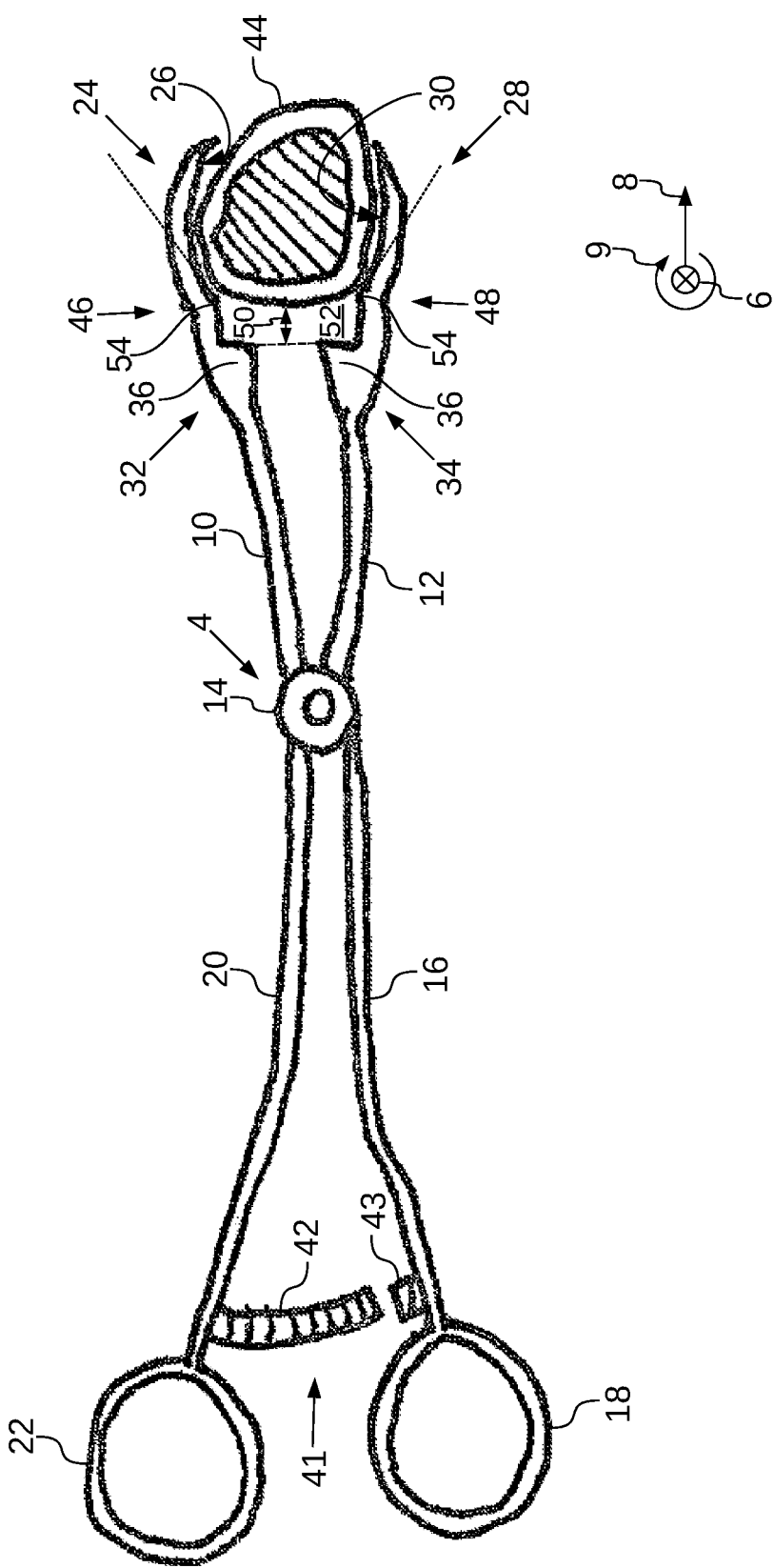
Figure 3:
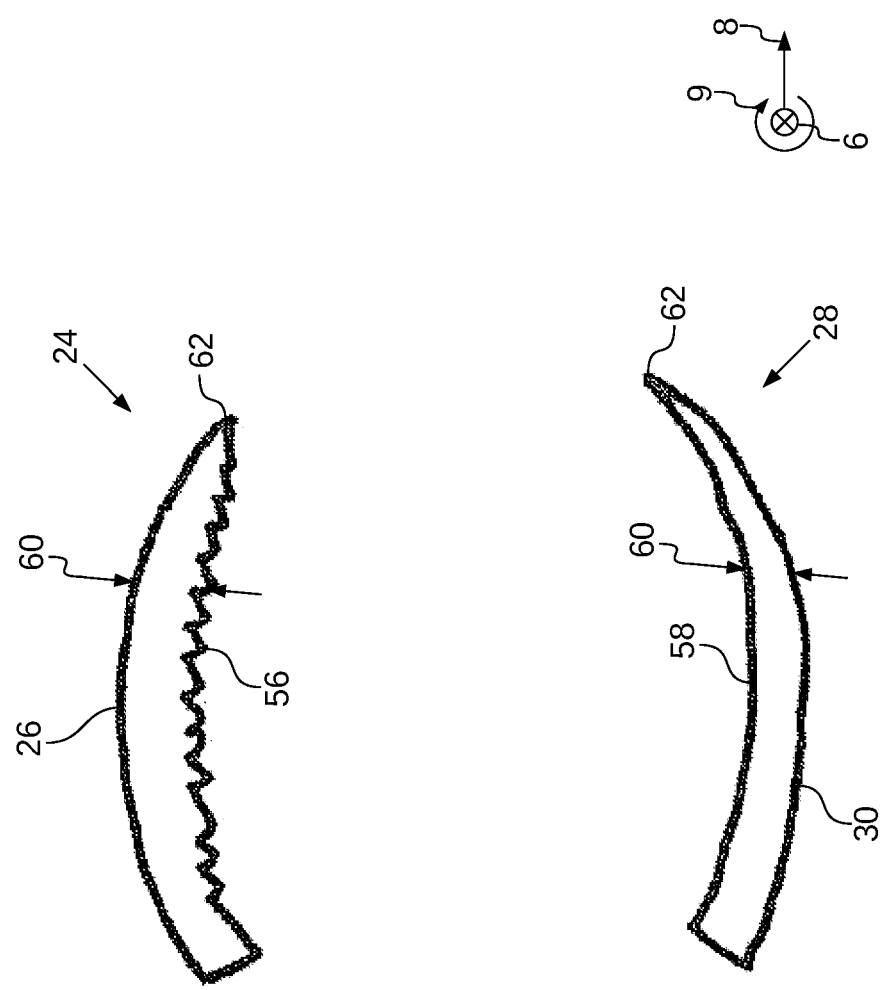
Figure 4:
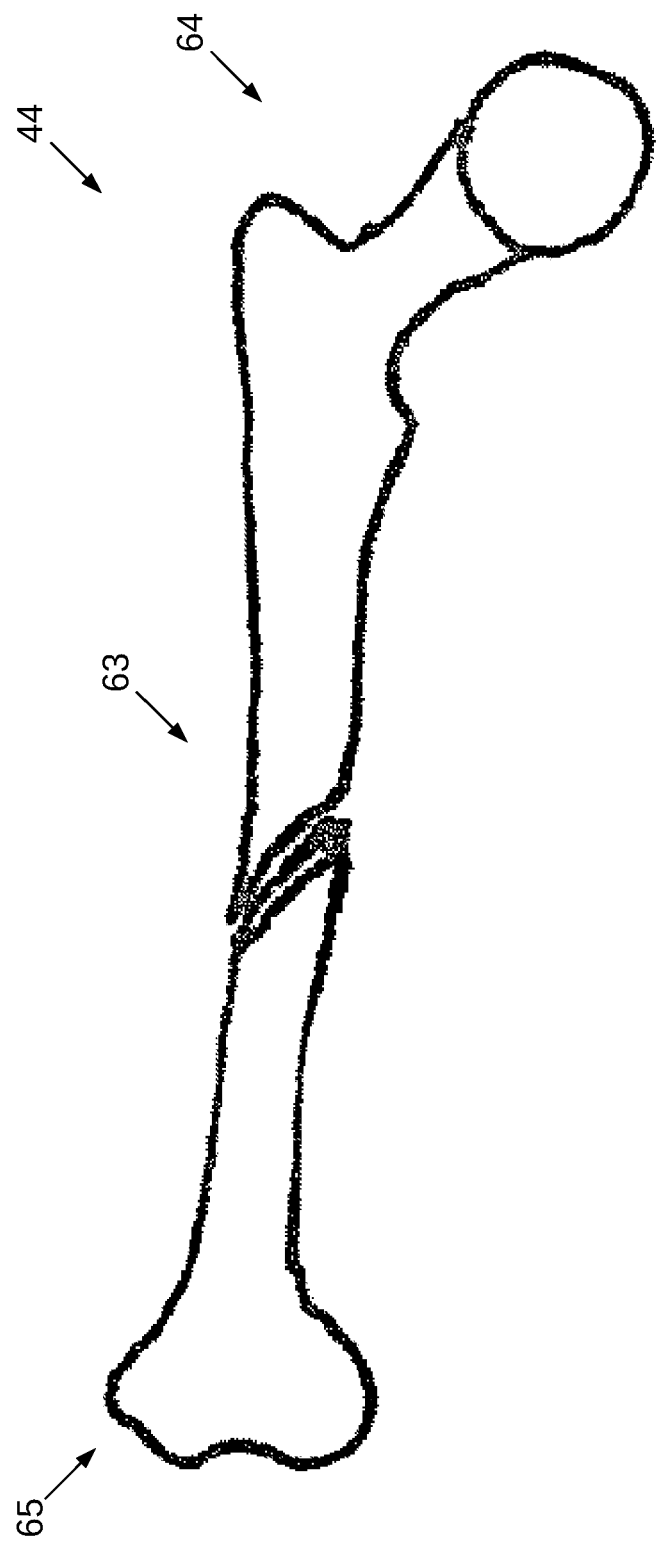
Figure 5:
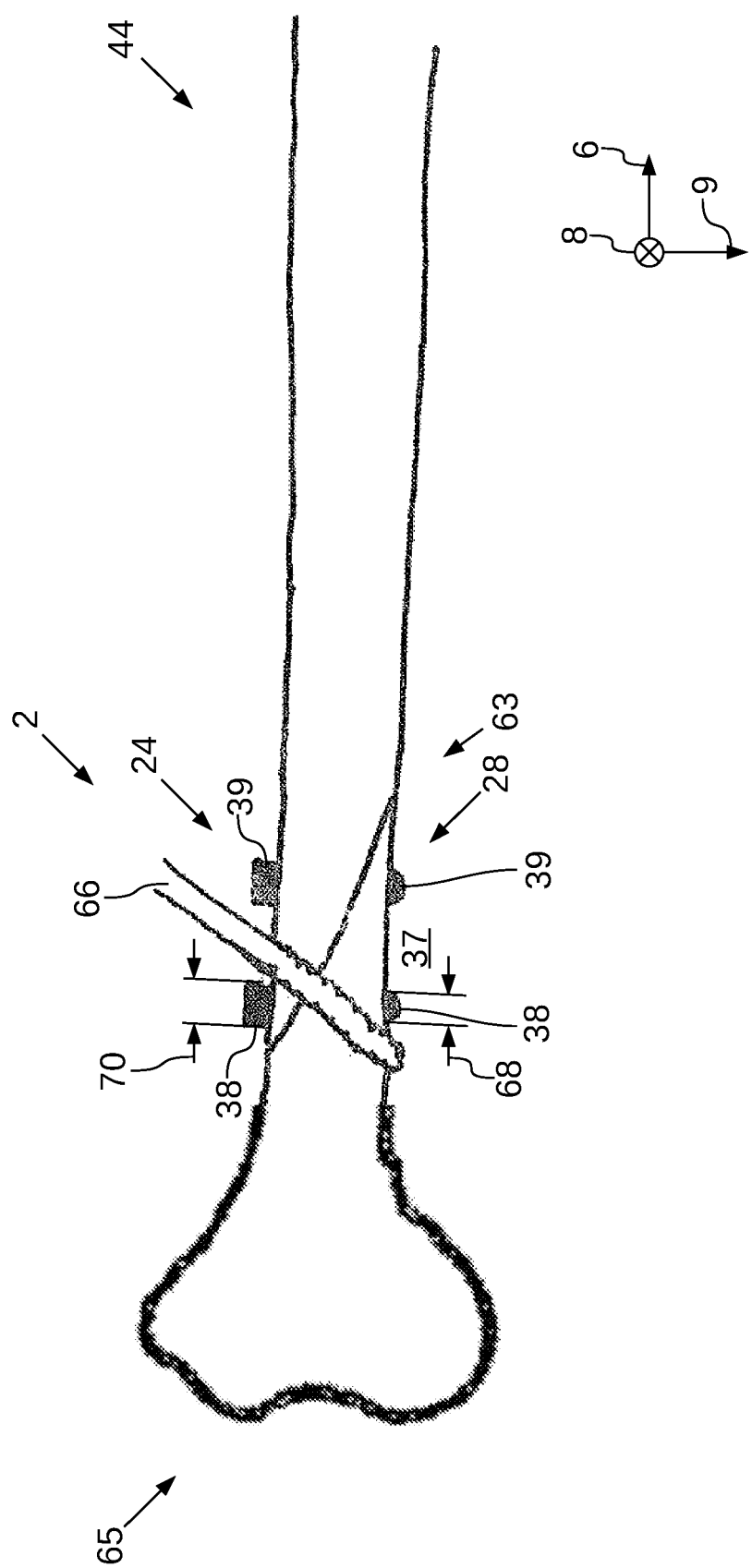
Figure 6:
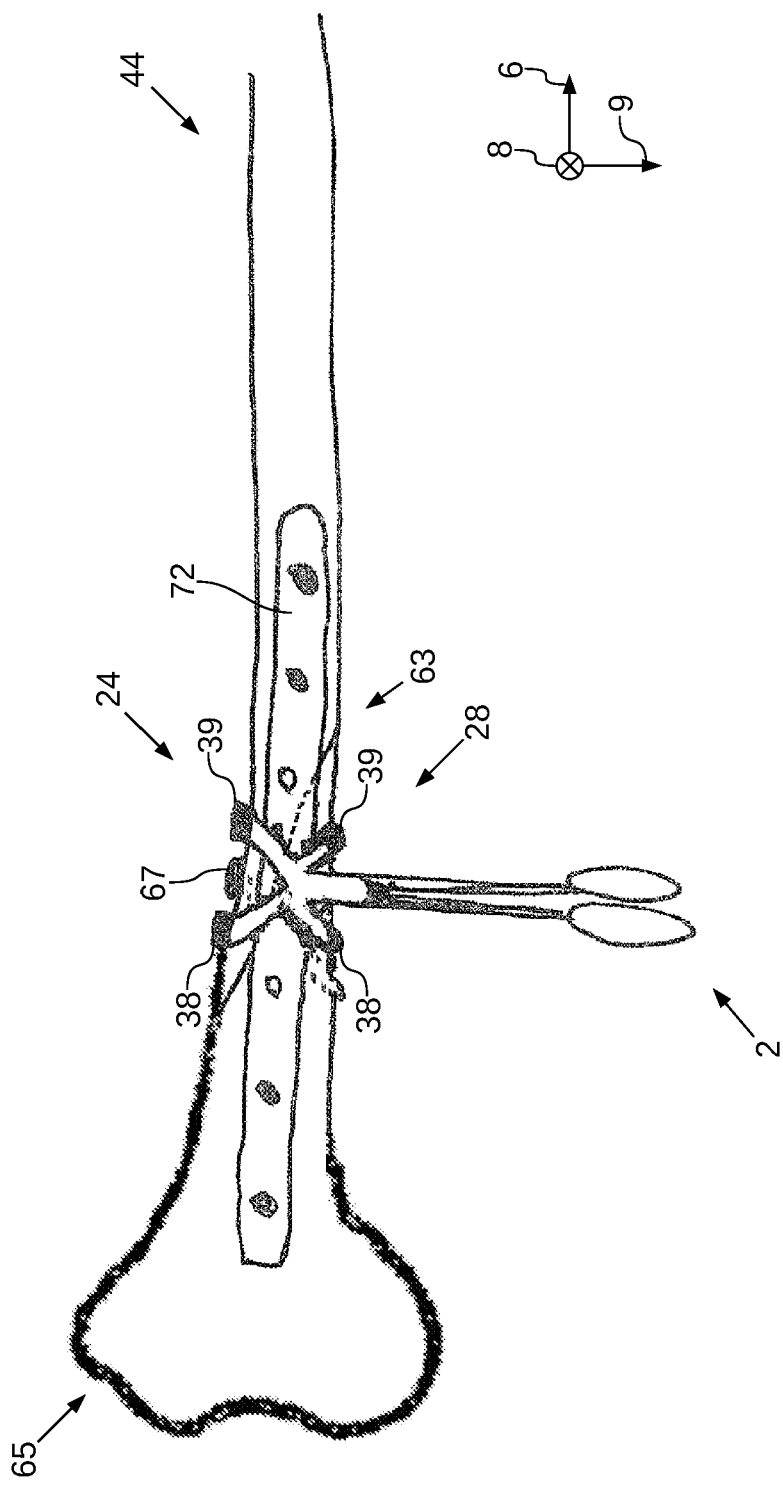
Figure 7:
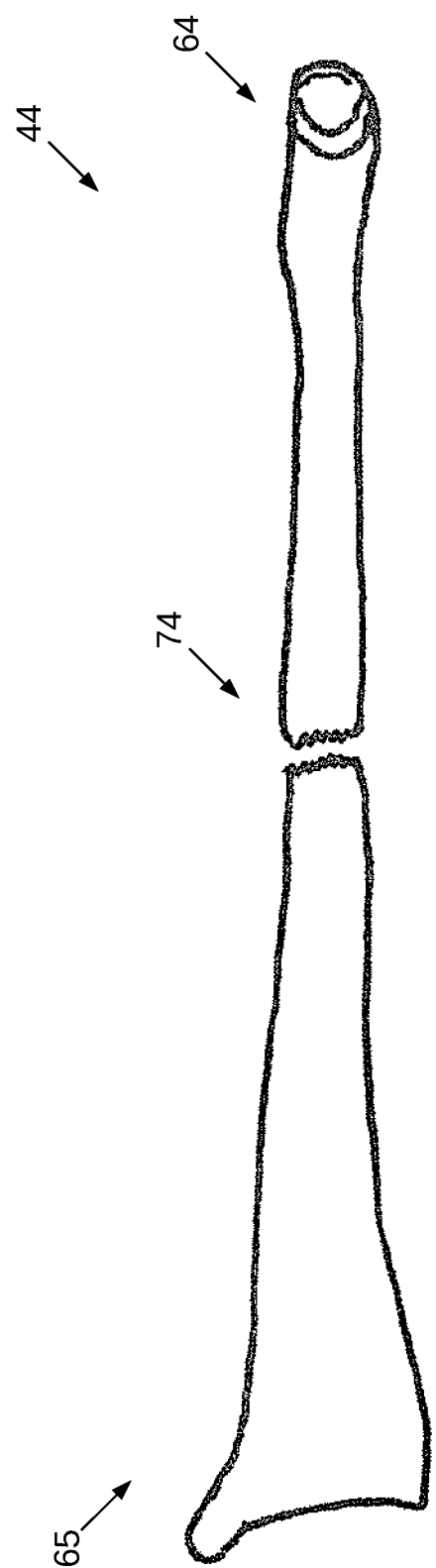
Figure 8:
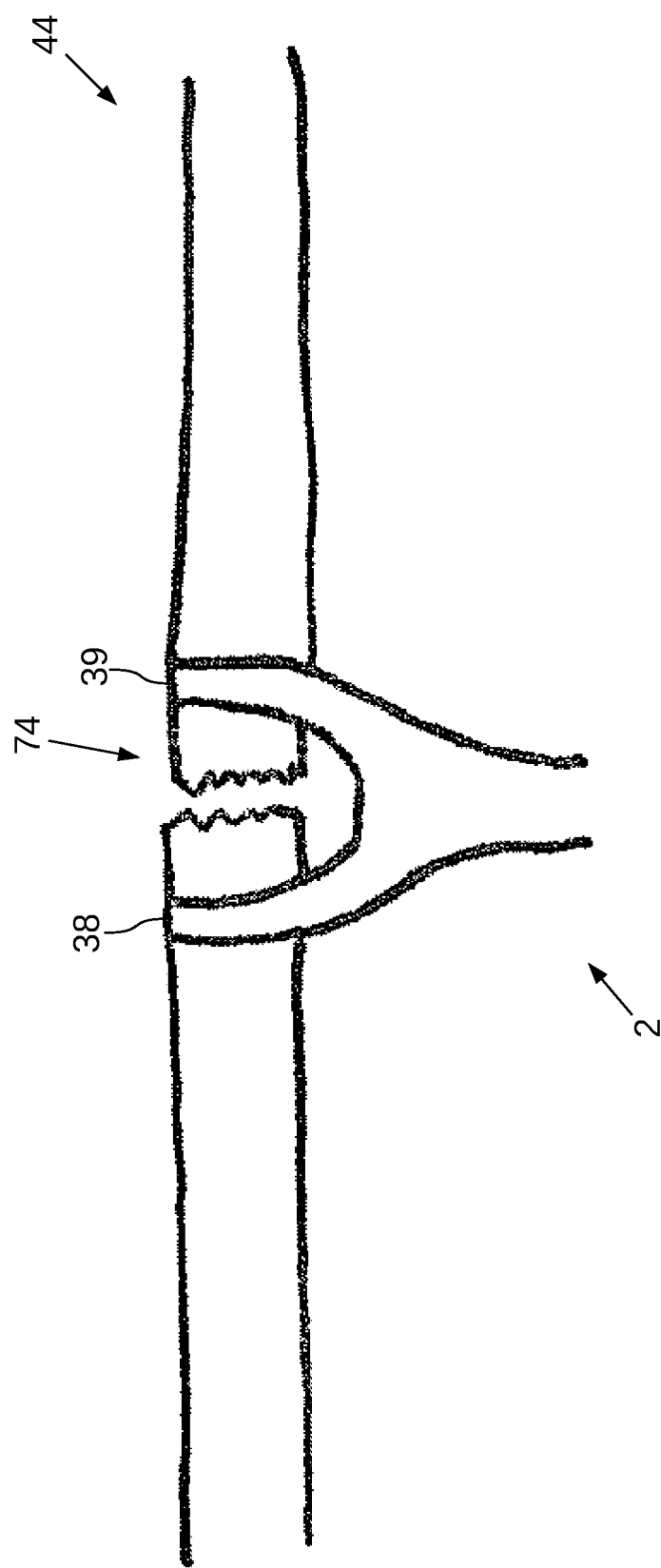

The above-described properties, features and advantages of this invention, as well as the manner in which they are achieved, will become clearer in connection with the following description of the embodiments, which are described in more detail in connection with the drawings, in which:

FIG. 1 shows a schematic view of a pair of surgical forceps in the form of repositioning forceps, FIG. 2 shows the repositioning forceps of FIG. 1 in an application state, FIG. 3 shows a schematic view of clamping sections of the repositioning forceps from FIG. 1, FIG. 4 shows a bone with an oblique rotational fracture, FIG. 5 shows the repositioning forceps from FIG. 1 on the bone of FIG. 4 from a first perspective, FIG. 6 shows the repositioning forceps from FIG. 1 on the bone of FIG. 4 from a second perspective, FIG. 7 shows a bone with a transverse fracture, and FIG. 8 shows the repositioning forceps from FIG. 1 on the bone of FIG. 7.

In the figures, the same technical elements are provided with the same reference signs, and are only described once. The figures are purely schematic and, in particular, do not reflect the actual geometric proportions.

Reference is made to FIG. 1, which shows a schematic view of surgical forceps, hereinafter referred to as repositioning forceps 2.

The repositioning forceps 2 is described below in a space which, from the viewpoint of a pivot point 4 still to be described, is spanned by an axial direction 6 pointing out of the image plane, a radial direction 8 extending transversely to the axial direction 6 in the image plane, and a direction of rotation 9 extending around the axial direction 6.

The repositioning forceps 2 comprises a first forceps part 10 extending in the radial direction 8 and a second forceps part 12 extending in the radial direction 8, which is rotatably held on the first forceps part 10 in the direction of rotation 9 about the pivot point 4 via a lock 14. The first forceps part 10 is adjoined by a first shank 16 having a first grip element 18, while the second forceps part 12 is adjoined by a second shank 20 having a second grip element 22. In the present embodiment, the repositioning forceps 2 are designed as hinged forceps, which is why the shanks 16, 20 with the grip elements 18, 22 adjoin the forceps parts 10, 12 on a side opposite the lock 14. If the repositioning forceps 2 were designed as clamp forceps, the shanks 16, 20 with the grip elements 18, 22 would be located between the forceps parts 10, 12 and the lock 14. Even though the invention is shown using the example of hinged forceps, it is not limited to such forceps.

The first forceps part 10 has, in the radial direction 8, also referred to as the longitudinal direction, a first forceps head 24 with a first clamping section 26 at an end opposite the lock 14, while the second forceps part 12 has, in the radial direction 8, at an end opposite the lock 14, a second forceps head 28 with a second clamping section 30 which cannot be seen in the perspective of FIG. 1. The two clamping sections 26, 30 are directed towards each other in the direction of rotation 9. In this way, a bone can be clamped between the forceps heads 24, 28 at the clamping sections 26, 30, which will be discussed in more detail later.

According to the invention, the first forceps part 10 comprises a first shoulder 32 extending in the axial direction 6 between its clamping section 26 and the lock 14, while the second forceps part 12 comprises a second shoulder 34 extending in the axial direction 6 between its clamping section 30 and the lock 14. A plate for osteosynthesis can be applied to the shoulders 32, 34 against the radial direction and thus pressed against a bone together with the repositioning forceps 2 in the radial direction 8. This will be described in more detail later.

In the present embodiment, the shoulders 32, 34 are each formed by two projections 36. One of the projections 36 is not visible in the perspective of FIG. 1 and is therefore only indicated by dashed lines.

Each forceps head 24, 28 has in its clamping section 26, 30 a recess 37 running counter to the radial direction 8, which separates the respective clamping section 26, 30 into a first fork tine 38 and a second fork tine 39.

A locking mechanism 41 is arranged between the shanks 16, 20 and the grip elements 18, 22. The locking mechanism 41 includes a toothed jaw 42 extending away from the second shank 20 in a direction opposite to the direction of rotation 9, while a locking tooth 43 engaging the toothed jaw 42 extends away from the first shank 16 in the direction of rotation 9. Between seven and twelve teeth are formed on the toothed jaw 42 with which the locking tooth 43 can positively engage in the direction of rotation 9 and position the forceps parts 10, 12 in a fixed manner relative to one another in predetermined angular positions.

Further details of the repositioning forceps 2 are discussed below with reference to FIG. 2, which shows the repositioning forceps 2 of FIG. 1 in an application state in which a bone 44 is clamped between the two clamping sections 26, 30.

The repositioning forceps 2 comprises a first spacer 46 at the first forceps part 10 between the first clamping section 26 and the first shoulder 32, while it comprises a second spacer 48 at the second forceps part 12 between the second clamping section 30 and the second shoulder 34. The two spacers 46, 48 are configured to maintain the bone 44 at a minimum distance 50 in front of the shoulders 32, 34. In this way, the spacers 46, 48 create a space 52 in which the above-described plate for osteosynthesis can not only be received but can still be properly positioned even after the bone 44 has been clamped.

In the present embodiment, the spacers 46, 48 are edges 54 formed by the clamping sections 26, 30 diverging from the shoulders 32, 34 as viewed in the radial direction 8 to form the edges 54 extending in the axial direction 6. The divergence is indicated by dashed lines in FIG. 2.

Before the use of the repositioning forceps 2 is discussed in more detail, the clamping sections 26, 30 of the repositioning forceps 2 from FIG. 1 will be discussed below with reference to FIG. 3.

In the present embodiment, the first clamping section 26 has knurls 56 on its side abutting the bone 44 to prevent slippage of the bone 44 when the bone 44 is clamped between the clamping sections 26, 30. In contrast, the surface 58 of the second clamping section 30, which is in contact with the bone 44, is smooth and allows precise positioning in the radial direction before the bone 44 is clamped. However, in principle, both clamping sections 24, 28 can be designed with the knurls 56 or both clamping sections 24, 28 can be designed smooth.

Both clamping sections 24, 26 are formed flat, that is, with a small thickness 60 in the direction of rotation 9. In addition, both clamping sections 24 are each formed with a sharp tip 62 at their ends directed away from the lock 14. In this embodiment, the repositioning forceps 2 can engage the bone 44 in a manner that is gentle on the tissue.

The use of the repositioning forceps 2 is explained in more detail below with reference to two examples.

First, the use of the repositioning forceps 2 for operating on an oblique rotational fracture is explained. For this purpose, reference is made to FIG. 4, which shows the bone 44 with an oblique rotational fracture 63.

The bone 44 of FIG. 5 is a femoral bone with a proximal end 64 directed toward the upper body and a distal end 65 directed toward the foot.

The operation of this oblique rotational fracture 63 with the repositioning forceps 2 will be explained in more detail below with reference to FIGS. 5 and 6.

Once the two bone parts of the bone 44 not further referenced are positioned against each other, the bone 44 is clamped between the forceps heads 24, 28 of the repositioning forceps 2 as shown in FIG. 5.

A hole is then drilled with a drill 66 in preparation for screwing in a lag screw 67 shown in FIG. 6. The drill 66 is placed between the two fork tines 38, 39 of the first forceps head 24 and driven through the bone 44 in the recess 37 as perpendicularly as possible to the oblique rotational fracture 63, so that the drill 66 exits the bone 44 again outside the second forceps head 28.

In order to ensure this as reliably as possible, the fork tines 38, 39 of the second forceps head 28, viewed in the axial direction 6, are formed with a width 68 which is smaller than a width 70 of the fork tines 38, 39 of the first forceps head 24.

Following the bore, the lag screw 67 can then be screwed in. Parallel to this, the plate for osteosynthesis, which is marked with the reference sign 72 in FIG. 5, can be inserted into the above-mentioned space 52. After the plate 72 is positioned and fixed with screws not further referenced, the repositioning forceps 2 can be released again. Other tools besides the repositioning forceps 2 are not necessary for the repositioning of the bone 44 and the positioning of the plate for osteosynthesis during the operation of the oblique rotational fracture 63. If necessary, other tools may be required for other operations, such as a soft tissue holding tool.

In the same way, the repositioning forceps 2 can also be used to operate on a transverse fracture 74, which is indicated on a forearm bone in FIGS. 7 and 8.

What is claimed:

1. Surgical forceps (2) configured to hold two bone parts of a fractured bone (44) at a bone fracture site (63, 74) comprising a first forceps part (10) extending in a radial direction (8) and a second forceps part (12) extending in the radial direction (8) rotatably held in a rotational direction (9) about a pivot (6) via a lock (14) on the first forceps part (10), each forceps part (10, 12) having a forceps head (24, 28) with a clamping section (26, 30) at one end in the radial direction (8) such that the each forceps part (10, 12) is configured to the clamp bone parts between the forceps heads (24, 28) at the clamping sections, the each forceps part (10, 12) has a shoulder (32, 34) between the clamping sections (26, 30) and the lock (14), extending transversely to the radial direction (8) and transversely to the direction of rotation (9), against which a plate (72) can be placed against the radial direction (8) for osteosynthesis of the bone parts;

wherein each forceps head (24, 28) has, in the region of its clamping section (26, 30), a recess (37) which runs counter to the radial direction (8) and separates the clamping section (26, 30) into a first fork tine (38) and a second fork tine (39), and wherein the first and second fork tines (38, 39) of one clamping section (26, 30) are thinner than the fork tines (38, 39) of the other clamping section (26, 30), as viewed transversely to the radial direction (8) and transversely to the direction of rotation (9); and the first and second fork tines (38, 39) are elastic in the direction of rotation (9) with a modulus of elasticity between 30 GPa and 100 GPa.

2. Surgical forceps (2) according to claim 1, comprising a spacer (46, 48) in at least one clamping section (26, 30) in front of the shoulder (32, 34) as seen in the radial direction (8), which is arranged to maintain a predetermined minimum distance (50) between the bone parts and the shoulder (32, 34).

3. Surgical forceps (2) according to claim 2, wherein the spacer (46, 48) is formed by the at least one clamping section (26, 30) diverging regionally in front of the shoulders (32, 34) as viewed in the radial direction (8).

4. Surgical forceps (2) of claim 1, wherein the shoulders (32, 34) are formed as projections (36) directed towards each other between the at least one clamping section (26, 30) and the lock (14).

5. Surgical forceps (2) according to claim 4, wherein at least two projections (36) are arranged next to each other for forming the shoulder (32, 34) of the at least one clamping section (26, 30).

6. Surgical forceps (2) according to claim 1, wherein the first and second fork tines (38, 39) are arranged on a side opposite the screw-in side of a fixing screw (67) for osteosynthesis of the bone parts.

7. Surgical forceps (2) according to claim 1, wherein the first and second fork tines (38, 39) are tapered in the radial direction (8).

8. Surgical forceps (2) of claim 1, wherein the clamping sections (26, 30) differ in their surface roughness.

* * * * *